United States Patent [19]  [11] 4,325,866
Bohn  [45] Apr. 20, 1982

[54] PROTEIN, PP$_{11}$, A PROCESS FOR ITS PREPARATION AND ITS USE

[75] Inventor: Hans Bohn, Marburg an der Lahn, Fed. Rep. of Germany

[73] Assignee: Behringwerke Aktiengesellschaft, Marburg an der Lahn, Fed. Rep. of Germany

[21] Appl. No.: 207,184

[22] Filed: Nov. 14, 1980

[30] Foreign Application Priority Data

Nov. 17, 1979 [DE] Fed. Rep. of Germany ....... 2946458

[51] Int. Cl.$^3$ .................... A61K 39/395; C07G 7/00
[52] U.S. Cl. .................. 260/112 B; 260/112 R; 424/12; 424/85; 424/88; 424/101
[58] Field of Search ...................... 260/112 B, 112 R; 424/12, 85, 88, 101

[56] References Cited

U.S. PATENT DOCUMENTS 4,041,021  8/1977  Bohn ............................... 424/12 X
4,191,533  3/1980  Bohn et al. ..................... 424/101 X
4,217,339  8/1980  Bohn et al. ................. 260/112 B X
4,269,825  5/1981  Bohn et al. ................. 260/112 R X Primary Examiner—Howard E. Schain
Attorney, Agent, or Firm—Curtis, Morris & Safford

[57] ABSTRACT

What are disclosed are a new protein, PP$_{11}$, obtainable from placental tissue, methods for isolating the protein in concentrated form, methods for making an antiserum to said protein, and methods for using said antiserum for monitoring pregnancy and for detecting and monitoring tumors and/or their therapy.

5 Claims, No Drawings

PROTEIN, PP₁₁, A PROCESS FOR ITS PREPARATION AND ITS USE

The invention relates to a new protein ($PP_{11}$) and a process for its preparation.

The subject of the invention is the protein $PP_{11}$, which is characterized by (a) a carbohydrate content of 3.9±0.9%, consisting of 2.6±0.5% of hexoses, 1.0±0.3% of hexosamines, 0.05±0.03% of fucose and 0.26±0.07% of neuraminic acid;

(b) a sedimentation coefficient $S_{20,w}^0$ of 3.5±0.2 S (c) a molecular weight of 44,300±6,000, determined in an ultracentrifuge;

(d) a molecular weight of 62,000±3,000, determined in polyacrylamide gel containing sodium dodecyl-sulfate (SDS);

(e) an extinction coefficient $E_1 \ _{cm}^{1\%}$ (280 nm) of 13.4±1.0, and (f) an electrophoretic mobility similar to that of the $\alpha_1$-globulins.

The following data are given to explain the characterizing features of the protein:

The sedimentation coefficient was determined in an analytical ultracentrifuge from Messrs. Beckman (Spinco apparatus, model E) at 60,000 rpm, in double-sector cells, with the aid of the UV-scanner technique at 280 nm. A 0.05 M phosphate buffer (pH 6.8) containing 0.2 mole/liter of NaCl was used as the solvent. The protein concentration was adjusted to give an optical density of about 3. The sedimentation coefficient was coverted to apply to water at 20° C.

The sedimentation equilibrium method was used to determine the molecular weight in the ultracentrifuge. In this method, the concentration of the protein was adjusted to give an optical density of about 1.0. The determination was carried out at 9,000 rpm. Recording was carried out with UV optical equipment at 280 nm, using the photoelectric scanner.

A gel of 7.5% of polyacrylamide (PAA) containing 0.1% of sodium dodecyl-sulfate (SDS) was used to determine the molecular weight in SDS-PAA gel. Human placentol lactogen (HPL) and human albumin and its aggregates, were used as the comparison substance.

To measure the extinction coefficient, the substance was dissolved in distilled water to give a concentration of 0.10%.

The electrophoretic mobility was determined, in the micro-scale modification, with the microzone R 200 instrument from Beckman Instruments, on cellulose acetate films (Messrs. Sartorius) using sodium diethylbarbiturate buffer of pH 8.6.

The carbohydrates were determined in accordance with the method described by H. E. Schultze, R. Schmidtberger and H. Haupt, Biochem. Z. 329, 490 (1958).

The aminoacid analysis was carried out in accordance with the method of S. Moore, D. H. Spackmann and W. H. Stein, Anal. Chem. 30, 1185 (1958), using the multichrome B liquid chromatography instrument from Messrs. Beckman. Cystine was determined as cysteic acid after oxidation of the protein with performic acid [S. Moore et al., Anal. Chem. 238, 235 (1963)]. The tryptophan content was directly determined photometrically in accordance with the method of H. Edelhoch, Biochemistry, 6, 1948 (1967).

Table I contains the result of the aminoacid analysis of $PP_{11}$.

TABLE I

Aminoacid composition of $PP_{11}$
(residues per 100 residues in mole %)

| | | Coefficient of variation % |
|---|---|---|
| Lysine | 6.26 | 7.00 |
| Histidine | 3.34 | 1.72 |
| Arginine | 3.31 | 5.60 |
| Aspartic acid | 10.75 | 2.43 |
| Threonine | 3.31 | 10.49 |
| Serine | 9.63 | 1.84 |
| Glutamic acid | 13.81 | 2.09 |
| Proline | 4.10 | 4.68 |
| Glycine | 6.23 | 6.26 |
| Alanine | 6.30 | 1.82 |
| Cystine ½ | 3.37 | 4.53 |
| Valine | 4.53 | 5.40 |
| Methionine | 1.00 | 26.22 |
| Isoleucine | 3.60 | 2.24 |
| Leucine | 6.74 | 1.05 |
| Tyrosine | 5.90 | 3.02 |
| Phenylalanine | 6.06 | 2.52 |
| Tryptophan | 1.66 | 20.87 |

$PP_{11}$ has the following properties, which can be used for its isolation.

(1) With ammonium sulfate, it is precipitated from aqueous solutions at pH 7.0 and 30–60% saturation.

(2) With water-soluble acridine bases, for example 2-ethoxy-6,9-diaminoacridine lactate (Rivanol(R)), it is precipitated at pH values of between 4 and 9 and at a concentration of the base of 0.2 to 0.8% w/v.

(3) Under the conditions of euglobulin precipitation, that is to say by adjusting the pH value to 5–6 in a dilute buffer solution, it is not precipitated.

(4) In preparative electrophoresis, its mobility is similar to that of the $\alpha_1$-globulins.

(5) In gel filtration with Sephadex(R), it behaves in the same way as proteins having molecular weights of 30,000 to 90,000.

(6) It can bind to weakly basic ion exchangers, such as, for example, DEAE-cellulose or DEAE-Sephadex, at a conductivity of about 0–2 mS and a pH value of about pH 7 to 9.

(7) It can be concentrated and isolated from an aqueous solution by immunoadsorption.

A further subject of the invention is a process for obtaining $PP_{11}$ which comprises fractionating a solution containing this protein utilizing the above-mentioned properties.

In addition to ammonium sulfate, it is of course possible to precipitate the $PP_{11}$ using other neutral salts conventionally employed in preparative biochemistry. In addition to an acridine base, a water-soluble derivative of a quinoline base, such as are known for protein fractionations, can also be employed within the scope of the process according to the invention. The protein can also be isolated according to its electrophoretic behavior as well as its molecular weight using other measures which are suitable for separating an $\alpha_1$-globulin from other proteins. The various methods of gel filtration, gel chromatography or ultrafiltration, or also the property of $PP_{11}$ whereby it can bind to weakly basic ion exchangers and can be eluted again therefrom, can also be used for this purpose.

The $PP_{11}$ can be isolated by means of an appropriate combination of the said measures, which have the effect of concentrating the $PP_{11}$ or separating this protein from other proteins.

Accordingly, the subject of the present invention is to be regarded as being the individual steps for concentrating $PP_{11}$, and the process for purifying $PP_{11}$ which results from a combination of the concentration measures.

The concentration process comprises using at least one of the aforementioned measures 1 to 6 or their chemical or biochemical preparative equivalents.

A further subject of the invention is a process for the preparation of $PP_{11}$ which comprises subjecting a liquid containing this protein to one or more procedures which are known for the isolation of proteins and in each case obtaining the material in which the protein having the features of $PP_{11}$ is present.

In addition to the parameters indicated, immunochemical methods can also be used to detect and determine the $PP_{11}$ which may be present in a fraction resulting from a separating operation, because $PP_{11}$ has antigenic properties.

An antiserum which can be used for this purpose can be obtained in the following manner: by immunizing rabbits with a placental protein fraction containing $PP_{11}$ [mother liquors resulting from the crystallization of human placenta lactogen (HPL) in accordance with the method of H. Bohn, Experientia 27, 1223 (1971)], a polyvalent antiserum is obtained with which $PP_{11}$ can be detected. By absorption with normal human serum and those placenta fractions which do not contain $PP_{11}$, or with proteins, for example HPL, this antiserum can be made extensively specific against the antigen $PP_{11}$. This specific antiserum can be used on the one hand for the immunological detection of $PP_{11}$ and on the other hand for the preparation of an immunoadsorbent which can be employed for concentrating and isolating $PP_{11}$.

The Ouchterlony gel diffusion technique (compare Schultze and Heremans, Molecular Biology of Human Proteins, Volume 1, page 134) can be used for the immunological detection of $PP_{11}$.

With the aid of the $PP_{11}$ obtained in accordance with the present application, monospecific antisera can be prepared by immunizing animals in accordance with known methods. $PP_{11}$ has antigenic properties. When animals are immunized with this protein, specific antibodies are formed. The detection and the determination of $PP_{11}$ using immunological methods is of diagnostic importance, on the one hand for monitoring pregnancy and on the other hand for detecting tumors, especially trophoblastic but also non-trophoblastic tumors, and also for monitoring the course of the illness and for monitoring the therapy in such diseases.

$P_{11}$ can therefore be used to prepare antisera which can be used to detect and determine $PP_{11}$.

The invention is illustrated in the following example:

Example (A) Extraction of placentos and fractionation of the extract with Rivanol and ammonium sulfate 1,000 kg of deep-frozen human placentos are comminuted in a cutting mixer and extracted with 1,000 liters of a 0.4% (w/w) sodium chloride solution. After the tissue residue has been separated by centrifugation, the extract is adjusted to pH 6.0 with 20% (w/w) acetic acid, and 200 liters of a 3% (w/w) solution of 2-ethoxy-6,9-diaminoacridine lactate (Rivanol$^{(R)}$, Hoechst AG) are added thereto, while stirring. 500 liters of a 2% (w/w) NaCl solution are added to the precipitate separated by centrifugation, the mixture is stirred for 4 hours and the precipitated 2-ethoxy-6,9-diaminoacridine chloride is centrifuged off. Solid ammonium sulfate is added slowly to the solution, while stirring, until an end concentration of 30% (w/v) is achieved, whereupon $PP_{11}$ precipitates together with other proteins. The precipitate is centrifuged off. This yields about 4.5 kg of a moist paste which will hereafter be referred to as fraction A.

(B) Gel filtration on Sephadex G-150

1,500 g of fraction A are dissolved in water and dialyzed against a 0.01 M tris-HCl buffer (pH 8.0) containing 0.05% of $NaN_3$ (buffer solution I). The solution which remains is transferred onto a column (60×56 cm) filled with Sephadex G-150 and eluted with buffer solution I. The eluates are tested in the Ouchterlony gel diffusion test using a specific anti-$PP_{11}$ rabbit serum. The fractions containing $PP_{11}$ are combined and referred to as fraction B.

(C) Chromatography on DEAE-cellulose

Fraction B is adsorbed onto DEAE-cellulose (10×28 cm column). The column is rinsed with buffer solution I and eluted with 0.85% (w/v) sodium chloride solution until no further precipitation occurs in the runnings with trichloroacetic acid. The proteins are precipitated from the eluate by adding ammonium sulfate until the concentration is 30% (w/v). The precipitate is centrifuged off (fraction C).

(D) Euglobulin precipitation

Fraction C is dissolved in water and dialyzed against buffer solution I. The solution is adjusted to pH 5.5 by adding 2 N acetic acid, while stirring. The precipitate, which substantially contains only concomitant proteins, is centrifuged off. The supernatant is dialyzed against a 0.1 M tris-HCl buffer solution of pH 8, containing 1 mole/liter of NaCl and 0.1% of sodium azide (buffer solution II) (fraction D).

(E) Concentration of $PP_{11}$ by immunoadsorption

1. Preparation of the immunoadsorbent 450 ml of an anti-$PP_{11}$ rabbit serum are dialyzed against 0.02 M phosphate buffer (pH 7.0) and chromatographed on DEAE-cellulose in order to separate the immunoglobulins. The immunoglubulin fraction (6.28 g of protein) is then reacted with 628 g of specially purified agarose in bead form (Sepharose$^{(R)}$ from Pharmacia, Uppsala, Sweden) which has been activated with 78.5 g of cyanogen bromide, and is thus covalently bonded to a carrier. The process has been described by R. Axen, J. Porath and S. Ernbach, Nature 214, 1302 (1967). With the aid of an immunoadsorbent prepared in this way, $PP_{11}$ can be isolated from its solutions, in particular from $PP_{10}$-enriched placental extract fractions.

2. Immunoadsorption.

The immunoadsorbent is suspended in buffer solution II, the suspension is filled into a chromatography column (6×20 cm) and the column is rinsed with buffer solution II. 40 ml of fraction B are then allowed to run slowly through the column, $PP_{11}$ becoming immunoadsorptively bound. The column is rinsed thoroughly with buffer II and the adsorbed protein is eluted with about 600 ml of 3 M potassium thiocyanate solution. The eluates containing $PP_{11}$ are dialyzed against buffer solution II and concentrated to about 10 ml using an ultrafilter. Yield per adsorption ~25 mg of $PP_{11}$.

Immediately after the elution of $PP_{11}$, the adsorbent in the column is neutralized again with buffer solution II and washed thoroughly; it can then be employed again for the immunoadsorptive binding of $PP_{11}$.

(F) Final purification of $PP_{11}$

The protein obtained by immunoadsorption is frequently contaminated by unspecifically bound serum proteins and other placental tissue proteins. The major part of the concomitant serum proteins is separated off, for example by gel filtration on Sephadex G-150. The remaining concomitant proteins are then removed by reverse or negative immunoadsorption, that is to say with the aid of carrier-bound antibodies against the proteins still present as impurities, namely immunoglobulin (IgG), $\beta_2$-glycoprotein III, $PP_{10}$ and $PP_{12}$.

I claim:

1. A protein, $PP_{11}$, extracted from placental tissue, having
   (a) a carboydrate content of 3.9±0.9%, consisting of 2.6±0.5% of hexoses, 1.0±0.3% of hexosamines, 0.05±0.03% of fucose and 0.26±0.07% of neuraminic acid;
   (b) a sedimentation coefficient $S_{20,w}^0$ of 3.5±0.2 S
   (c) a molecular weight of 44,300±6,000, determined in an ultracentrifuge;
   (d) a molecular weight of 62,000±3,000, determined in polyacrylamide gel containing sodium dodecylsulfate (SDS);
   (e) an extinction coefficient $E_1{}_{cm}^{1\%}$ (280 nm) of 13.4±1.0, and
   (f) an electrophoretic mobility similar to that of the $\alpha_1$-globulins.

2. A process for concentrating the protein extracted from placental tissue, having
   (a) a carbohydrate content of 3.0±0.9%, consisting of 2.6±0.5% of hexoses, 1.0±0.3% of hexosamines, 0.05±0.03% of fucose and 0.26±0.07% of neuraminic acid;
   (b) a sedimentation coefficient $S_{20,w}^0$ of 3.5±0.2 S;
   (c) a molecular weight of 44,300±6,000, determined in an ultracentrifuge;
   (d) a molecular weight of 62,000±3,000, determined in polyacrylamide gel containing sodium dodecylsulfate (SDS);
   (e) an extinction coefficient $E_1{}_{cm}^{1\%}$ (280 nm) of 13.4±1.0, and
   (f) an electrophoretic mobility similar to that of the $\alpha_1$-globulins,
which comprises subjecting a solution containing this protein to at least one of the following measures and obtaining the fraction enriched in $PP_{11}$:
   (a) precipitation with ammonium sulfate in the pH range of 5 to 8 and at 30–60% saturation,
   (b) precipitation with a water-soluble acridine base at a pH value of between 4 and 9 and at a concentration of 0.2–0.8% (w/v),
   (c) separation of concomitant proteins by means of euglobulin precipitation at a pH value of 5–6 in a dilute salt solution,
   (d) preparative zone electrophoresis and recovery of the $\alpha_1$-globulin fraction,
   (e) gel filtration in order to obtain proteins in the molecular weight range from 30,000 to 90,000,
   (f) adsorption on weakly basic ion exchangers and elution of the protein or
   (g) immunoadsorptive concentration.

3. A process for isolating a protein, extracted from placental tissue, having
   (a) a carbohydrate content of 3.9±0.9%, consisting of 2.6±0.5% of hexoses, 1.0±0.3% of hexosamines, 0.5±0.03% of fucose and 0.26±0.07% of neuraminic acid;
   (b) a sedimentation coefficient $S_{20,w}^0$ of 3.5±0.2 S;
   (c) a molecular weight of 44,300±6,000, determined in an ultracentrifuge;
   (d) a molecular weight of 62,000±3,000, determined in polyacrylamide gel containing sodium dodecylsulfate (SDS);
   (e) an extinction coefficient $E_1{}_{cm}^{1\%}$ (280 nm) of 13.4±1.0, and
   (f) an electrophoretic mobility similar to that of the $\alpha_1$-globulins, which comprises subjecting a liquid containing the protein to at least one known procedure for isolating proteins and, in each instance, recovering that material containing the protein to be isolated.

4. The method of making an antiserum to the protein of claim 1 which comprises immunizing an animal with the protein of claim 1 and recovering serum containing antibodies to said protein.

5. An antiserum made by the method of claim 4.

* * * * *